United States Patent [19]

Munson

[11] 4,177,830
[45] Dec. 11, 1979

[54] VALVE ASSEMBLY PERMITTING INDEPENDENT PEAK FLOW AND DECAY RATE CONTROL OF PERIODIC GAS FLOWS

[75] Inventor: Ramon J. Munson, Rialto, Calif.

[73] Assignee: Bourns, Inc., Riverside, Calif.

[21] Appl. No.: 752,945

[22] Filed: Dec. 21, 1976

[51] Int. Cl.² .......................... F16K 31/12; A62B 7/00
[52] U.S. Cl. ............................... 137/501; 128/205.24
[58] Field of Search ........................... 137/501, 116.5; 128/145.8, 145.6, 147.2

[56] References Cited

U.S. PATENT DOCUMENTS

| 2,608,209 | 8/1952 | Bryant | 137/501 |
| 2,879,783 | 3/1959 | Taplin | 137/116.5 |
| 2,917,069 | 5/1960 | Lundy et al. | |
| 2,936,152 | 5/1960 | Renick | 137/501 |
| 2,951,501 | 9/1960 | Thylefors | 137/501 |
| 2,998,021 | 8/1961 | Becker | 137/116.5 |
| 3,100,620 | 8/1963 | Kates | |
| 3,100,620 | 8/1963 | Kates | 137/501 |
| 3,351,086 | 11/1967 | Baker | |
| 3,554,221 | 1/1971 | McMurry et al. | |
| 3,677,288 | 7/1972 | Martin | 137/501 |
| 3,773,296 | 11/1973 | McKendrick | 137/116.5 |
| 3,820,566 | 6/1974 | Sundblom et al. | 137/624.14 |

*Primary Examiner*—Martin P. Schwadron
*Assistant Examiner*—A. Michael Chambers
*Attorney, Agent, or Firm*—Paul H. Ware; William G. Becker

[57] ABSTRACT

The valve assembly employs a peak flow valve with a first adjustable orifice which restricts gas flow through a conduit to establish a peak flow, a peak flow control for adjusting the size of the orifice, a separate valve which progressively closes a second conduit orifice in response to increases in the conduit pressure so as to achieve a desired decay rate for periodic gas flow, and a decay rate control which adjusts the initial closure of the second orifice. The valves are interconnected by means of a coupling which, in response to the decay rate control being adjusted, automatically adjusts the size of the first orifice by an amount sufficient to substantially compensate for changes in the peak flow rate caused by the decay rate adjustment.

10 Claims, 8 Drawing Figures

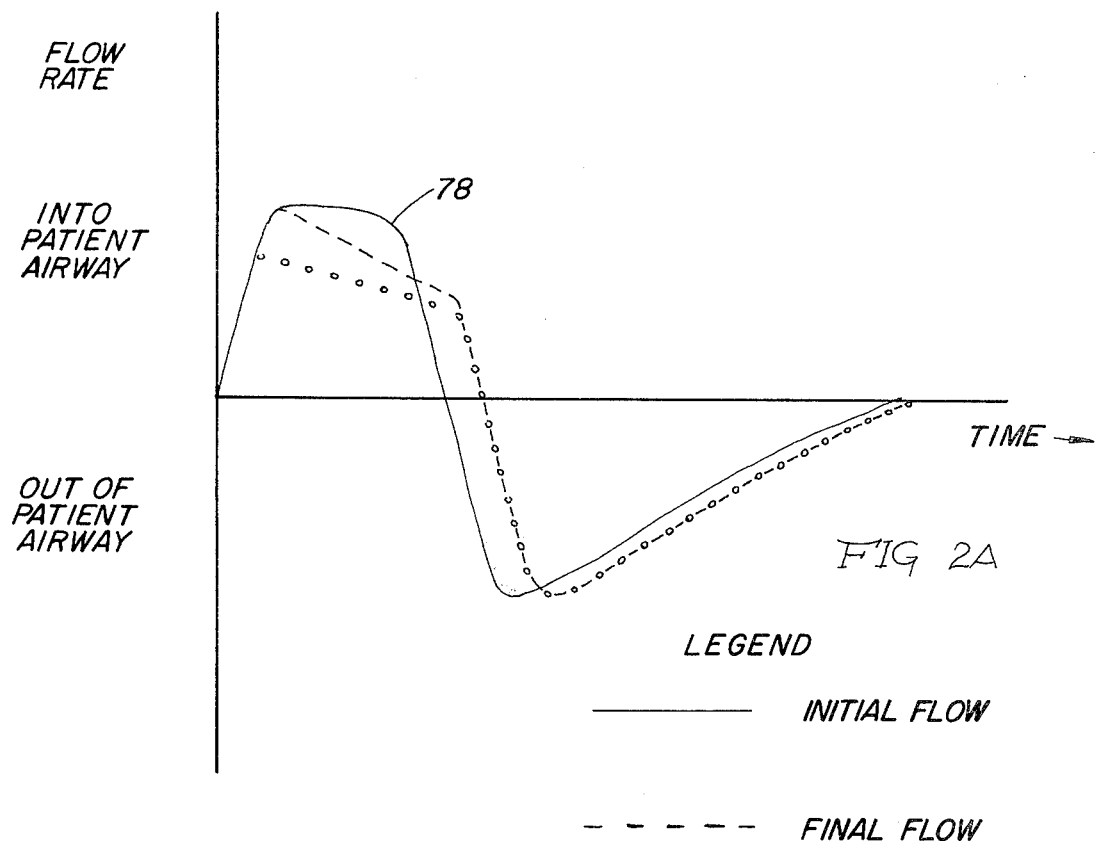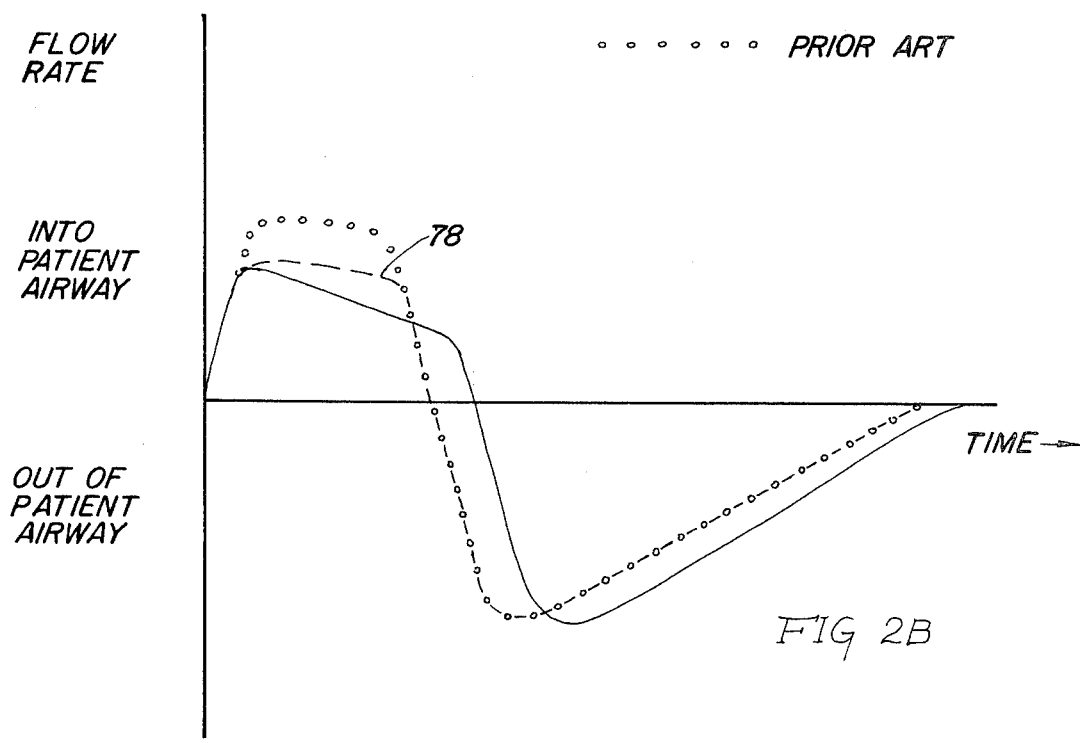

VALVE ASSEMBLY PERMITTING INDEPENDENT PEAK FLOW AND DECAY RATE CONTROL OF PERIODIC GAS FLOWS

BACKGROUND OF THE INVENTION

This invention relates to pneumatic valves, and more particularly to a combined peak flow and decay rated valve assembly suitable for use in a medical respirator.

It is of great importance in respirator therapy to carefully control the gas flows to avoid injuring the patient and to ensure that a maximum therapeutic effect is achieved. To this end various flow control valves are normally installed in the conduit system which connects the respirator air supply with the patient. One of these valves is typically a peak flow control which restricts the maximum volumetric flow of gas to the patient to a predetermined amount, in order to avoid expanding the patient's lungs beyond a safe and prudent level. The peak flow rate is normally reached during an early stage of inspiration, followed by a gradually decreasing intake of air until the patient is ready to exhale. Another valve is frequently employed to control the rate at which the inspiratory air flow tapers off, with the optimum decay rate depending upon the type of therapy administered. The decay rate valve normally employs a separate restriction in the air flow conduit, which restriction varies in inverse proportion to the pressure in the conduit leading to the patient. Thus, as the pressure in the patient conduit increases, indicating that the patient's air needs are being satisfied, the decay rate restriction drops and partially nullifies the decrease in flow rate that would otherwise accompany the increase in patient pressure. By an appropriate selection of the initial decay rate restriction, the decay rate can be controlled from a rapid decay to an almost square wave characteristic in which the air flow remains near the maximum flow level until the end of the inspiration is approached. For example, if a rapid decay is desired, the decay rate valve would be set to a fairly high initial restrictive value. If a slow decay is desired, the valve is set to a fairly low initial restrictive value which permits a greater increase in conduit pressure before significantly closing the conduit.

While the above decay rate valve does enhance the overall control which can be be achieved, it also introduces an additional restriction in the flow line which can effect the maximum flow level in undesired ways. In the case of a high initial restriction, in addition to having the desired effect on the decay rate the valve would also increase the total restriction in the patient supply conduit so as to reduce the peak flow value. To avoid introducing an error into the peak flow valve, some compensating adjustment of the peak flow valve would then have to be made. Each time the decay rate valve is adjusted thereafter, the peak flow would be further altered.

Various valves are known which involve more than one flow restricter, and in which an alteration of one restricter changes the gas flow through the other. U.S. Pat. No. 2,608,209 to Bryant and U.S. Pat. No. 2,951,501 to Thylefors disclose valves which are designed to provide a constant volumetric flow despite variations in input pressure. In each of these patents a manually adjustable downstream valve is used to establish a desired flow rate, while a spring or diaphragm-biased upstream valve filters out incoming pressure variations. The two valves act independently of each other, and only the downstream valve is adjustable.

U.S. Pat. No. 2,917,069 to Lundy et al discloses another type of valve which is both rotatably and axially adjustable by separate controls. Coarse adjustments are made by rotating the valve, followed by a fine adjustment made by moving the valve axially. A somewhat similar concept is utilized in patent application Ser. No. 677,344 filed Apr. 15, 1976 and assigned to the assignee of the present invention. In this invention a cylindrical valve is manually rotated to adjust the gas flow level, while the rotatable part is affixed to a diaphragm for axial movement which restricts the valve opening when the flow rate decreases. The object of the latter invention is to maintain a substantially constant pressure drop across the valves despite variations in flow rate.

While each of the above patents and patent application disclose multiple valve devices, none of them provides the combination of (a) a peak flow control and (b) a flow decay rate control which can be adjusted without altering the peak flow rate.

SUMMARY OF THE INVENTION

In light of the above problems associated with the prior art, the principal object of the present invention is the provision of a novel and improved valve assembly having both peak flow and flow decay rate control means, in which adjustment of the decay rate portion does not affect the peak flow rate.

Another object is the provision of a novel and improved peak flow/decay rate valve in which the peak flow rate can be adjusted by operating a single control, and the flow decay rate can also be adjusted without affecting the peak flow rate by operating another single control.

Still another object is the provision of a novel and improved dual valve control means having separate peak flow and decay rate restriction orifices, in which adjustment of the decay rate orifice automatically adjusts the peak flow orifice to compensate for changes that would otherwise occur in the peak flow rate.

In the accomplishment of these and other objects, apparatus is provided for independently controlling the peak volume and decay rates of periodic gas flows through a conduit. The apparatus includes a peak flow valve having a first adjustable orifice restricting the flow of gas through the conduit, and a control means which controls the peak flow rate by adjusting the size of the orifice. A decay rate valve includes a second orifice forming a portion of the conduit, means for progressively closing the second orifice in response to increasing pressure in the conduit so as to impose a predetermined decay rate on the gas flow, and a control means which sets the decay rate by adjusting the initial closure of the decay rate orifice. Changes in the peak flow rate resulting from adjustment of the decay rate control are compensated for by automatically adjusting the size of the first orifice in a counter direction.

In a preferred embodiment the peak flow valve includes a cylindrical member and a casing having mutually adjustable, alignable ports forming the first orifice. Both the peak flow and decay rate valves are provided with rotatable controls, and also with means for translating rotation of a control into a longitudinal valve adjustment movement. In addition, the decay rate control and the peak flow cylindrical member are coupled by a gear arrangement which rotates the cylindrical member when the decay rate control is operated. This in turn adjusts the alignment of the peak flow cylindrical member and casing ports by an amount sufficient to compensate for changes in peak flow resulting from adjustment of the decay rate valve.

DESCRIPTION OF THE DRAWINGS

Further advantages and features of the invention will be apparent to those skilled in the art from the ensuing detailed description thereof, taken together with the accompanying drawings, in which:

FIGS. 2a and 2b are graphs illustrating the regulation of patient air flow that can be achieved with the present invention, as compared with prior art devices;

DESCRIPTION OF A PREFERRED EMBODIMENT

Figure 1:
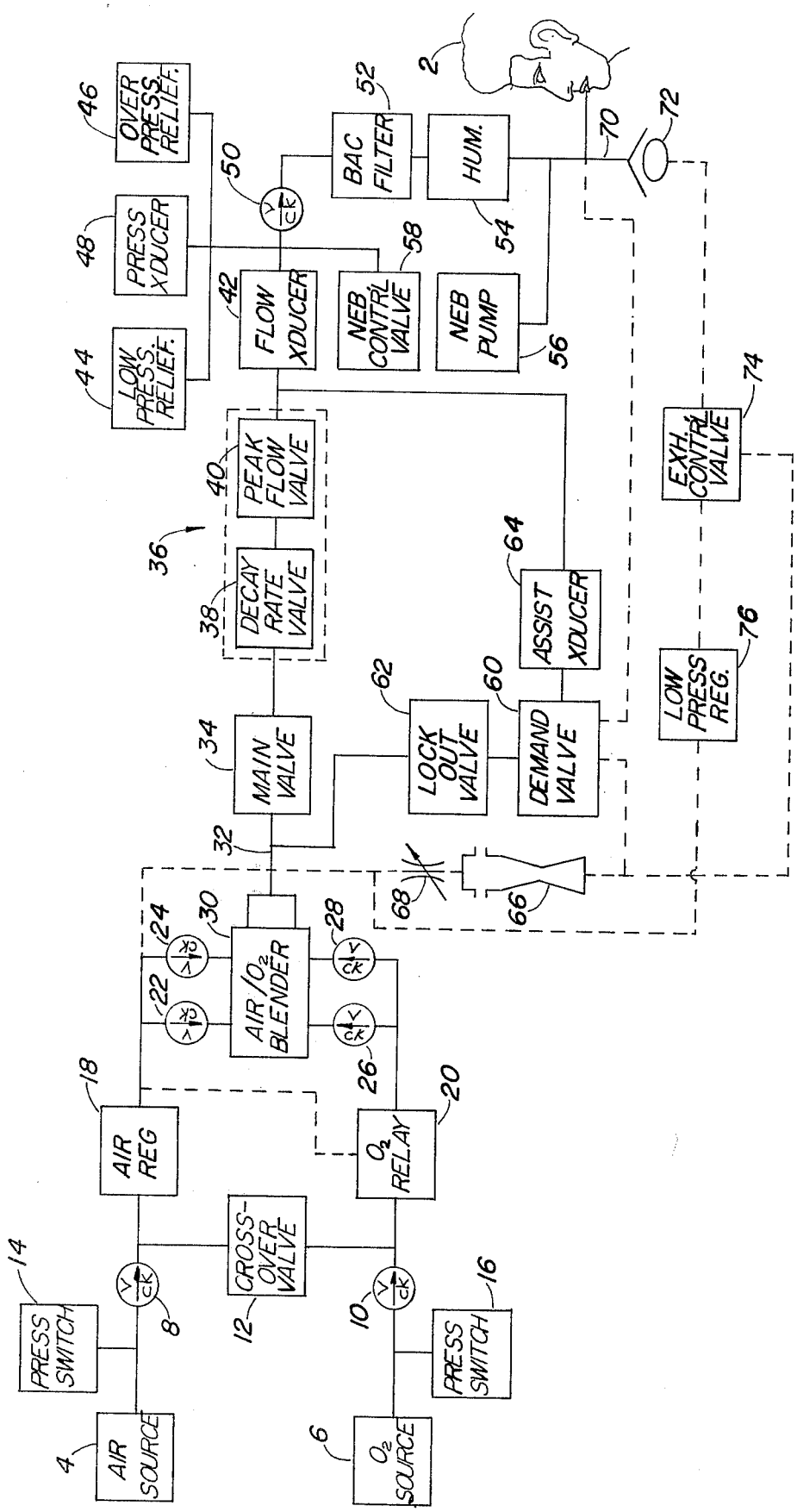
FIG. 1 is a schematic flow diagram showing a medical respirator in which the invention may advantageously be employed.

FIG. 1 illustrates the pneumatic operation of a medical respirator which employs the improved peak flow/decay rate valve of the present invention. Principal conduits which support the flow of breathing air to a patient 2 are indicated by solid lines, while pilot lines serving principally to establish pressures at various locations within the respirator are indicated in dashed lines. Starting from the left-hand side of the figure, ambient air and oxygen are delivered from appropriate sources 4 and 6 through check valves 8 and 10 to opposite sides of a cross-over valve 12, which is opened by pressure switches 14 and 16 in case one of the sources is lost to ensure that the patient receives at least some breathing air. A regulator 18 in the airline establishes a desired line pressure, typically about 10 psi, with a relay 20 in the oxygen line slaved to regulator 18 to keep the oxygen line at the same pressure. The air and oxygen are delivered through check valves 22, 24, 26, and 28 to a two-stage blender 30 which combines the input gases in desired proportions and supplies an outflow of breathing gas through conduit 32. Blender 30 employs a first stage which operates continuously and a second stage which operates only for large air flows, with the two stages combining to give accurate blending over a wide range of flow rates.

Continuing with the main air flow, conduit 32 branches with one branch going to a main valve 34. With a respirator having facilities for multiple modes of operation, valve 34 can be used in both a control mode, in which a predetermined volume of breathing gas is delivered to the patient at set intervals, and in an assist mode, in which the valve is opened by a patient's attempt to breathe rather than at fixed intervals. The valve output is processed through valve assembly 36, which forms the subject matter of this invention. Valve assembly 36 comprises a pair of independently controlled devices: a decay rate regulator or valve 38 which controls the rate at which periodic flows of breathing gas decay from a peak value, and a peak flow valve 40 which controls the maximum rate of flow to the patient. A flow transducer 42 downstream from valve asssembly 36 measures the gas volume delivered to the patient and closes main valve 34 when the desired volume has been delivered. Connected to the output of flow transducer 42 are low and high pressure relief valves 44 and 46, and a pressure transducer 48 which activates appropriate alarms for adverse pressure conditions. The output of flow transducer 42 is delivered to the patient through a check valve 50, bacteria filter 52, and humidifier 54. Various medications may be added to the breathing gas flow by a nebulizer pump 56, which is deactivated during patient exhalation by a control valve 58.

An alternate flow path from blender 30 is provided for a demand mode, i.e., a mode in which the respirator permits the patient to breathe on his own without delivering positive air flows. This path begins at the other branch of conduit 32 and includes a demand valve 60 which maintains the pressure in the system above a certain minimum amount to prevent the patient's lungs from becoming unduly depressurized, a lock-out valve 62 which locks out demand valve 60 in the control mode, and an assist transducer 64 which operates in the assist mode to detect breath attempts and actuate main valve 34 in response thereto. Assist transducer 64 is connected to the output of valve assembly 36 so that breathing air flows in all modes are treated for bacteria, humidity, and medications. Other aspects of the respirator include a venturi 66 with a variable orifice 68 for maintaining a positive pressure on demand valve 60 and thereby establishing a positive expiratory end pressure, an exhaust 70 for expired air, and an expandable bladder 72 which blocks exhaust 70 during patient inhalation and collapses during exhalation. Bladder 72 is operated by a three-way exhalation control valve 74 which connects the bladder to the regulated pressure of venturi 66 during expiration, and to a low pressure regulator 76, supplied by regulator 18, during inspiration.

Having described the general features of a respirator in which the subject peak flow/decay rate valve may be incorporated, it should be noted that the valve is not limited to such an application, but rather may be employed with other devices in which both peak flow and decay rate control are desired for periodic gas flows. FIGS. 2a and 2b illustrate the operating characteristics of the improved valve assembly, as contrasted with prior art valves. FIG. 2a illustrates the situation when it is desired to increase the decay rate of breathing air flow delivered to a patient. An assumed initial flow characteristic, indicated by a solid line, shows air flow to the patient decaying only slightly from an initial peak value until a break point 78 is reached, after which inhalation rapidly falls to zero. (Although the graph shows the air flow changing from a positive inhalation direction to a negative exhalation direction without interruption, in actuality a pause is frequently observed between the end of one inhalation and the beginning of the next exhalation, during which time there is substantially zero flow to or from the patient.) If it is now desired to increase the decay rate so that air flow to the patient decreases more steadily, a decay rate valve can be adjusted accordingly. For prior art devices, however, in which the decay rate valve operates independently of the peak flow valve, an increase in the air flow restriction presented by the decay rate valve increases the total flow restriction of both valves, thereby reducing the peak flow that can be processed by the valves. This situation is illustrated by a dotted line in FIG. 2a, in which an increase in the decay rate is accompanied by a decrease in the peak flow attained prior to decay. With the present invention the flow pattern follows the dashed line, reaching a peak flow substantially equal to the unadjusted flow before commencement of the rapid decay. The decay rate can thus be adjusted substantially independently of the peak flow rate.

The reverse situation, in which the decay rate is lowered from an initially high value, is illustrated in FIG. 2b. In this case prior art devices which reduce the flow restriction imposed by the decay rate valve without reference to the peak flow valve produce an undesired increase in the peak flow rate. With the present invention, on the other hand, a leveling off of the decay rate is achieved without materially affecting the peak flow rate.

Figure 3:
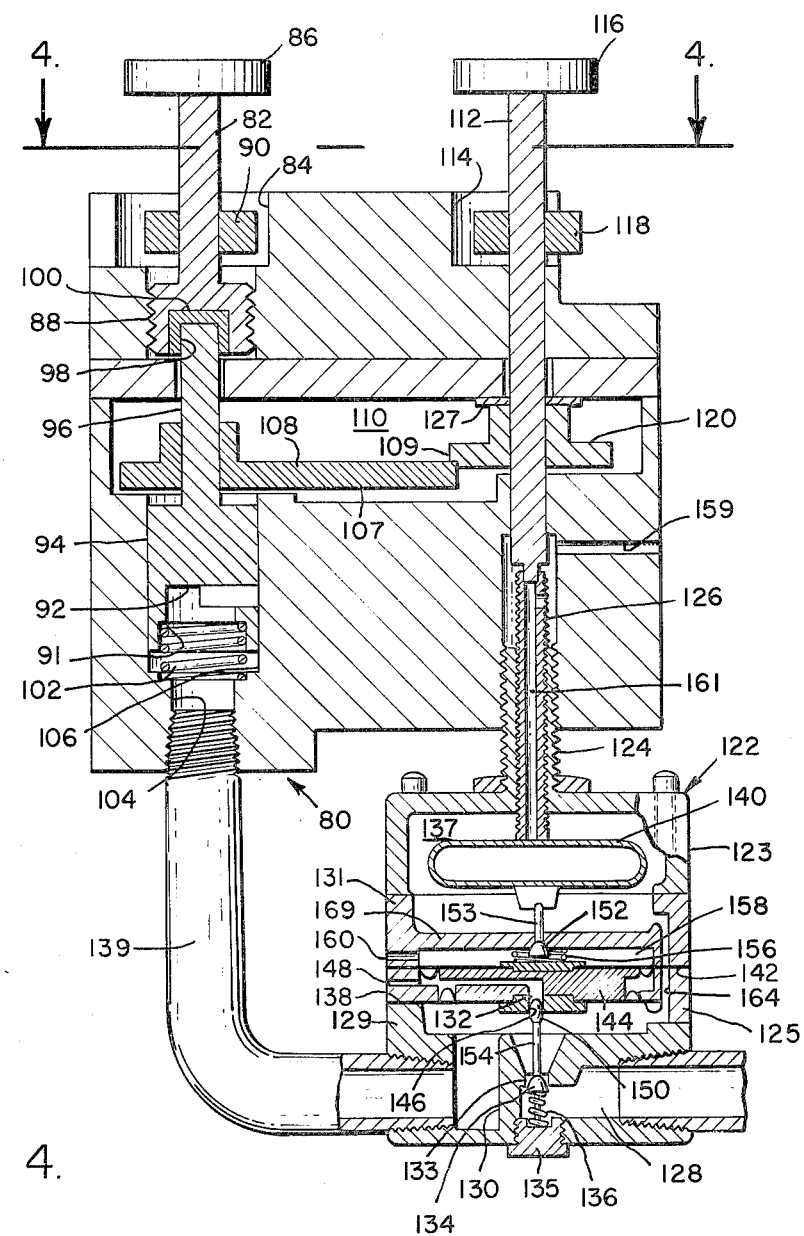
FIG. 3 is a sectional view of a combined peak flow/decay rate valve constructed in accordance with the present invention.

A preferred embodiment of apparatus which achieves the above flow characteristics is shown in FIGS. 3 through 6. Referring first to FIG. 3, the valves are contained in a metal housing generally indicated by numeral 80. The peak flow portion of the valve assembly includes a shaft 82 which extends into housing 80 through a bore 84 and has a knob 86 attached to its outer end for manipulation by the operator. At the lower end of shaft 82 is an externally threaded head 88 which engages threads on the interior of bore 84 to permit longitudinal shaft movement by rotating knob 86, while a stop collar 90 limits shaft rotation. Contained within an internal housing compartment 92 is a hollow cylindrical member 94 having an axially extending shaft 96 which projects into a recess 98 in the underside of control shaft head 88. A slip collar 100 is press-fit into recess 98 and abuts the upper surface of cylinder shaft 96 such that axial rotation of control shaft 82 imparts a longitudinal movement to cylinder 94, with the interior walls of collar 100 slipping against but not rotating the adjacent surface of cylinder shaft 96. A coil spring 102 is lodged between the bottom of compartment 92 and a downward facing axial shelf of cylindrical member 94 to return that member upward toward an initial position when control shaft 82 is rotated upward. The lower all of cylinder 94 is removed, permitting air to flow into the valve through an inlet port 104 and out through an outlet orifice 106 FIG. 5. Orifice 106 comprises a pair of alignable ports respectively in the cylinder wall and in the surrounding housing wall which forms a casing for the cylinder. The design of orifice 106 is an important feature of the invention and will be described in greater detail hereinafter.

Attached to an intermediate portion of cylinder shaft 96 is a gear member 107 having an arm 108 which extends through a cavity 110 in the housing and carries gear teeth 109 at its outer end which mesh with corresponding gear teeth 111 on the decay rate valve. A control for the decay rate valve includes a second shaft 112 extending into the housing through a second bore 114, an operating knob 116 at the outer end of the shaft, and a stop collar 118 limiting the shaft rotation. A rotary gear piece 120 is attached to shaft 112 within cavity 110, and is provided with teeth which mesh with the gear teeth of peak flow arm 108 such that rotation of decay rate shaft 112 imparts a corresponding rotation through the gear mechanism to peak flow shaft 82. The gear arrangement is shown in a perspective view in FIG. 5.

Figure 4:
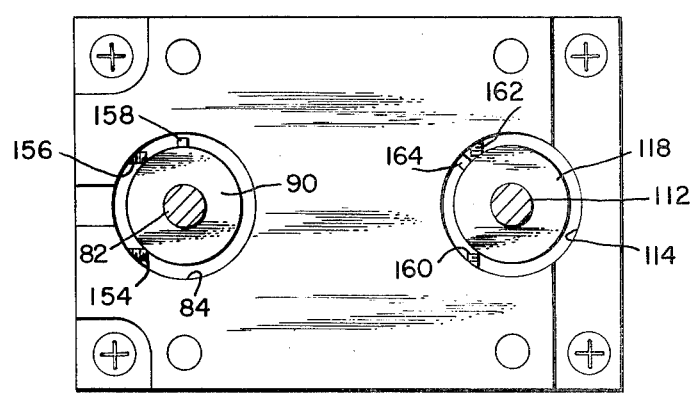
FIG. 4 is a plan view taken along the lines 4—4 of FIG. 3.

Referring now to FIG. 4 for further details of the valve controls, a pair of stops 154 and 156 are provided adjacent the periphery of stop collar 90 on the peak flow control, separated by an angular spacing of approximately 90°. A tab 158 extends out from collar 90 in the area of the larger, approximately 270° arc separating stops 154 and 156. Peak flow control shaft 82 can thus be rotated through an arc of approximately 270° in moving cylinder 94 FIG. 3 up and down. Similar stops 160 and 162 are provided at a 90° separation adjacent the periphery of stop collar 118 on the decay rate control. A tab 164 extends out from collar 118 within the shorter arc separating the two stops, limiting the rotation of decay rate shaft 112 to approximately 90°.

Figure 5:
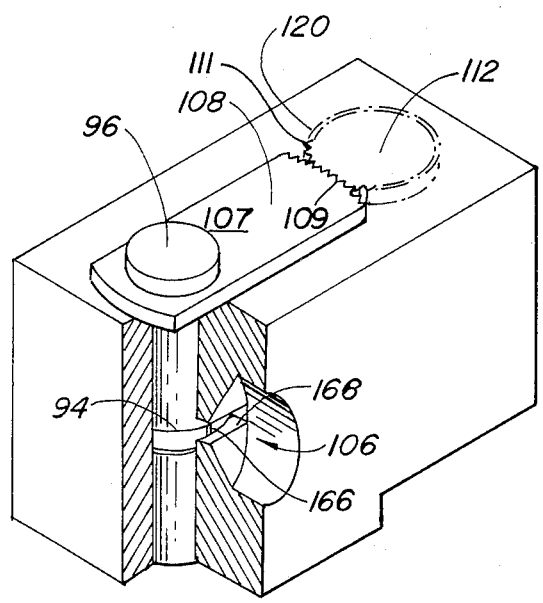
FIG. 5 is a cutaway view in perspective showing an interior portion of the valve assembly.
Figure 6:
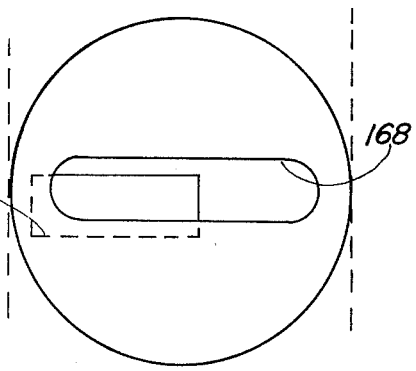
FIG. 6 is a fragmentary view of the peak flow valve orifice.

Details of peak flow orifice 106 are shown in FIG. 5 and also in FIG. 6. The orifice comprises the combination of a first port 166 in the side wall of cylinder 94, and a second port 168 in the portion of housing 80 which forms a casing for the cylinder. When aligned, the two ports 166 and 168 combine to form an orifice of maximum dimensions, permitting a maximum peak flow. Rotation of peak flow control shaft 82 FIG. 3 moves cylinder 94 longitudinally up or down to partially misalign the two ports, thus reducing the effective orifice area and also the peak flow rate. When decay rate control shaft 112 FIGS. 3 and 5 is rotated, imparting a rotation to cylinder 94 through the action of gear members 108 and 120, port 166 is moved laterally to further alter the orifice dimension. By an appropriate selection of dimensions for ports 166 and 168 relative to the decay rate valve and gear members 108 and 120, the effective area of peak flow control orifice 106 is automatically adjusted, in response to rotation of decay rate control shaft 112, to compensate for changes in the total restriction to peak flow which is attributable to the decay rate valve. In this manner the total peak flow restriction of the valve assembly can be maintained at a substantially constant level for a given setting of the peak flow valve, despite adjustments which may be made in the decay rate valve setting. For increased accuracy, gears 108 and 120 may be formed in cam shapes to optimize the correlation between adjustment of the decay rate valve and compensating adjustments of orifice 106.

Figure 7:
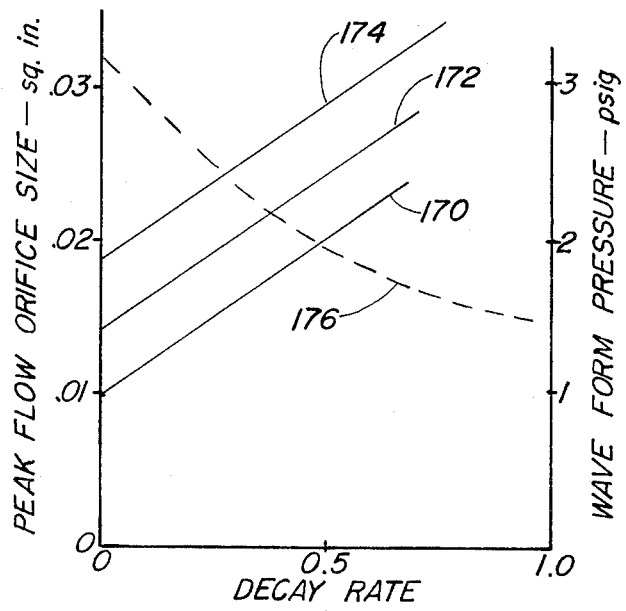
FIG. 7 is a graph illustrating the dependence of the peak flow orifice opening and the pressure presented to the peak flow valve upon the initial setting of the decay rate valve.

FIG. 7 is a graph plotting both the effective size of peak flow orifice 106 against flow decay rate, for various peak flow settings, and the pressure presented to the peak flow valve against flow decay rate. A decay rate of 1.0 indicates maximum taper of the decay rate curve while a decay rate of 0 would approach a square wave decay waveform. The orifice size scale is given on the left-hand vertical axis, and the peak flow pressure scale on the right-hand vertical axis. Referring first to the orifice size, line 170 illustrates the situation for a relatively low peak flow level, at which peak flow orifice 106 is relatively small. This is because ball 134 of the decay rate supply valve is offset appreciably from orifice 132 for low decay rates such that the decay rate valve presents a relatively small restriction to peak flows. As the decay rate increases, ball 134 is moved upward to increasingly block orifice 132 and create a greater resistance to peak flows. Peak flow orifice 106 is accordingly progressively opened by the gear mechanism to lower the resistance of the peak flow valve, and thereby compensate for the increase in peak flow resistance. Adjustment of the peak flow control to increase the peak flow setting moves cylinder 94 in a direction which increases the longitudinal alignment between ports 166 and 168, thereby increasing the size of orifice 106 and moving curve 170 upward on the graph to a position such as curve 172 or 174. If the decay rate valve is now adjusted, orifice 106 will continue to compensate for attendant changes that would otherwise be induced in the peak flow rate at the higher levels of flow.

Dashed line 176 relates the line pressure at inlet port 104 to the peak flow valve to various settings of the decay rate valve. It will be recalled that the decay rate valve creates restriction in the patient flow path, which restriction increases positively with decay rate. The pressure remaining for the peak flow valve for a given peak flow setting will accordingly vary inversely with the decay rate. With the compensating mechanism provided by the present invention, any such pressure change is balanced out by an adjustment of the peak flow orifice, the result being a net peak flow rate which is substantially independent of the decay rate.

Novel and improved apparatus for controlling the rate of periodic gas flows, while permitting independent adjustment of the peak flow and decay rates, is thus made available by the present invention. While a particular embodiment of the invention has been shown and described, numerous additional modifications and variations are possible in light of the above teachings. For example, the gear system illustrated above results in a linear relationship between decay rate adjustment and peak flow rate compensation. This design produces small inaccuracies in the compensation level over most of the adjustment range. Other mechanical linkages may be designed in which the peak flow compensation varies non-linearly with decay rate adjustment so as to keep the peak flow rate exactly constant over the entire decay rate adjustment range. It is therefore intended that the scope of the invention be limited only in and by the terms of the appended claims.

What is claimed is:

1. Apparatus for controlling the peak flow rates and decay rates of periodic gas flows through a conduit, the peak flow rates being characterized by an initial minimum pressure followed by a progressively increasing pressure, comprising:

a housing for retaining elements of said apparatus;
   an adjustable peak flow valve in said housing having an adjustable orifice for restricting the flow of gas through said conduit, said adjustable peak flow valve comprising
   a cylindrical aperture in said housing for retaining the elements;
   a hollow cylindrical member slideably situated within said aperture;
   an axially extending shaft formed integrally with one end of said hollow cylindrical member;
   an annular step forming an axial shelf at the other end of said hollow cylindrical member;
   a first port formed in a side wall of said hollow, cylindrical member;
   a second port, capable of alignment with said first port, formed in said housing;
   means to adjust said hollow, cylindrical member axially and rotatably to vary alignment of said first and said second ports; adjustment of said alignment of said ports forming said adjustable orifice;—and—adjustment of said adjustable orifice controlling peak flow through said conduit an adjustable decay rate valve in said housing having a regulator controlled by means of adjustments made to said adjustable decay rate valve, said regulator having means for receiving a supply of gas under pressure from an inlet port, said regulator means including means for sensing pressure at said peak flow valve, means for regulating said gas in response to the pressure at said peak flow valve adjustable orifice, and conduit means for supplying the regulated gas to said adjustable peak flow valve;
   means responsive to the adjustment of said adjustable peak flow valve for effecting adjustment of said adjustable decay rate valve;
   whereby said responsive adjustment means is responsive to adjustment of said adjustable decay rate valve for effecting the adjustment of said peak flow valve so as to automatically adjust the size of said orifice by an amount sufficient to substantially compensate for changes in the peak flow rate resulting from the adjustment of said adjustable decay rate valve.

2. The apparatus of claim 1, wherein said responsive adjustment means comprises means adjustably coupling said adjustable decay rate valve means with said adjustable peak flow valve means so as to compensate for changes in peak flow rate resulting from adjustment of said adjustable decay rate valve means, said coupling means being effective also to compensate for changes in decay rate resulting from adjustment of said adjustable peak flow valve means.

3. The apparatus of claim 2, wherein said means for adjustably restricting gas flow through said conduit comprises:

means subject to both rotational and axial adjustment further comprising:
   a cylindrical aperture in said housing for retaining the elements;
   a hollow, cylindrical member slideably situated within said aperture;
   an axially extending shaft formed integrally with one end of said hollow cylindrical member;
   an annular step forming an axial shelf at the other end of said hollow cylindrical member;
   a first port formed in a side wall of said hollow, cylindrical member;
   a second port, capable of alignment with said first port, formed in said housing for retaining the elements;
   means to adjust said hollow, cylindrical member including means to adjust said member axially with respect to said cylindrical aperture so as to vary alignment of said first and said second ports, and
   means to adjust said hollow, cylindrical member rotatably so as to vary alignment of said first and said second ports.

4. The apparatus of claim 3, wherein said means to adjust said hollow cylindrical member further comprise:

a first bore having an internal threaded portion, formed in said housing for retaining the elements;
   a first control shaft located in said first bore;
   a first stop collar also located in said first bore and secured to said first control shaft;
   a first operating knob joined to said first control shaft;
   an externally threaded head integrally formed with said first control shaft and threadedly operable with said internally threaded portion of said first bore;

a recess formed in said externally threaded head;

a slip collar press fit into said recess for slipably accepting said axially extending shaft formed integrally with one end of said hollow cylindrical member;

a coil spring bearing between the bottom of said cylindrical aperture in said housing for retaining the elements and said axial shelf at the other end of said hollow cylindrical member.

5. The apparatus of claim 4, wherein said means for controlling the decay rate of periodic gas flows through said conduit further comprise:

a second bore in said housing for retaining the elements;

a stepped, smaller bore extending from said second bore through said housing for retaining the elements;

an internally threaded lower portion of said smaller bore for threadedly attaching a regulator;

a second control shaft located in said second bore and said stepped smaller bore and extending therethrough to an inner adjustment shaft of a regulator;

a second operating knob joined to said second control shaft.

6. The apparatus of claim 5, wherein said means adjustably coupling said adjustable decay rate valve means with said adjustable peak flow valve means comprises:

a cavity formed in said housing for retaining the elements;

a laterally extending gear member having an arm and located in said cavity, attached at one of its ends to said axially extending shaft;

gear teeth formed at the other end of said gear member;

a rotary gear piece having gear teeth attached to said second control shaft and enmeshed with said gear teeth formed at the other end of said gear member.

7. The apparatus of claim 1, wherein said means to adjust said hollow, cylindrical member comprises:

a first bore having an internal threaded portion, formed in said housing for retaining the elements;

a first control shaft located in said first bore;

a first stop collar also located in said first bore and secured to said first control shaft;

a first operating knob joined to said first control shaft;

an externally threaded head integrally formed with said first control shaft and threadedly operable with said internally threaded portion of said first bore;

a recess formed in said externally threaded head;

a slip collar press fit into said recess for slipably accepting said axially extending shaft integrally with one end of said hollow cylindrical member;

a coil spring bearing between the bottom of said cylindrical aperture in said housing for retaining the elements and said axial shelf at the other end of said hollow cylindrical member.

8. The apparatus of claim 7, wherein said means responsive to adjustment of said adjustable peak flow valve for effecting adjustment of said adjustable decay rate valve comprise:

a cavity formed in said housing for retaining the elements;

a gear member situated within said cavity;

an arm, integral with said gear member, operably connected at one end to said axially extending shaft also situated within said cavity; and gear teeth formed at another end of said arm for engagement with said adjustable decay rate valve.

9. The apparatus of claim 1, wherein said adjustable decay rate valve further comprises:

a second bore in said housing for retaining the elements;

a stepped, smaller bore extending from said second bore through said housing for retaining the elements;

an internally threaded lower portion of said smaller bore for threadedly attaching said regulator;

a second control shaft located in said second bore and said stepped smaller bore and extending therethrough to an inner adjustment shaft of said regulator;

a second operating knob joined to said second control shaft.

10. The apparatus of claim 9, wherein said means responsive to adjustment of said adjustable decay rate valve comprise:

a cavity formed in said housing for retaining the elements;

a rotary gear piece attached to said second control shaft in said cavity for engagement with said adjustable peak flow valve;

a bowed thrust washer for maintaining positional integrity between said rotary gear piece and said inner adjustment shaft.

* * * * *